United States Patent [19]

Gordon et al.

[11] Patent Number: 4,848,167
[45] Date of Patent: Jul. 18, 1989

[54] SAMPLING APPARATUS

[75] Inventors: Norman R. Gordon, Kennewick; Lloyd L. King, Benton; Peter O. Jackson, Richland, all of Wash.; Alan W. Zulich, Bel Air, Md.

[73] Assignee: Battelle Memorial Institute, Richland, Wash.

[21] Appl. No.: 186,180

[22] Filed: Apr. 26, 1988

[51] Int. Cl.[4] ............................................. G01N 1/04
[52] U.S. Cl. ............................. 73/864.71; 73/863.86
[58] Field of Search ............ 73/863.86, 864, 864.71; 435/30, 292–295

[56] References Cited

U.S. PATENT DOCUMENTS

| | | | |
|---|---|---|---|
| 3,074,276 | 1/1963 | Moos | 73/864.71 |
| 3,308,039 | 3/1967 | Nelson | 435/295 |
| 3,513,830 | 5/1970 | Kalayjian | 435/295 |
| 3,554,039 | 1/1971 | Braun | 73/864.71 |
| 4,018,653 | 4/1977 | Mennen | |
| 4,223,093 | 9/1980 | Newman et al. | |
| 4,409,988 | 10/1983 | Greenspan | 435/295 |
| 4,479,393 | 10/1984 | Shores | 73/863.86 |
| 4,687,746 | 8/1987 | Rosenberg et al. | 435/292 |

FOREIGN PATENT DOCUMENTS 0058008 8/1982 European Pat. Off. ............ 435/295

Primary Examiner—Stewart J. Levy
Assistant Examiner—Robert R. Raevis
Attorney, Agent, or Firm—Wells, St. John & Roberts

[57] ABSTRACT

A sampling apparatus is provided for sampling substances from solid surfaces. The apparatus includes first and second elongated tubular bodies which telescopically and sealingly join relative to one another. An absorbent pad is mounted to the end of a rod which is slidably received through a passageway in the end of one of the joined bodies. The rod is preferably slidably and rotatably received through the passageway, yet provides a selective fluid tight seal relative thereto. A recess is formed in the rod. When the recess and passageway are positioned to be coincident, fluid is permitted to flow through the passageway and around the rod. The pad is preferably laterally orientable relative to the rod and foldably retractable to within one of the bodies. A solvent is provided for wetting of the pad and solubilizing or suspending the material being sampled from a particular surface.

32 Claims, 4 Drawing Sheets

U.S. Patent   Jul. 18, 1989   Sheet 1 of 4   4,848,167
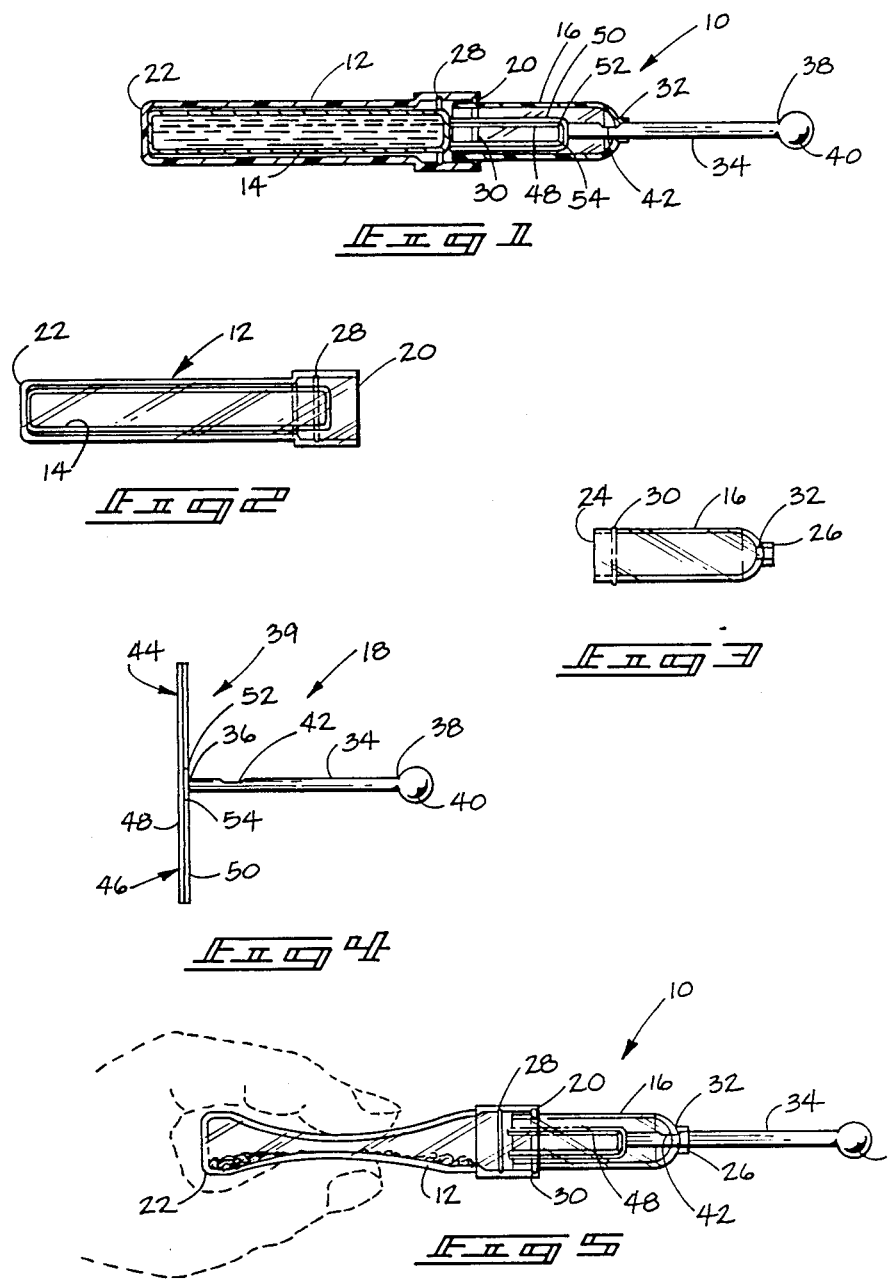

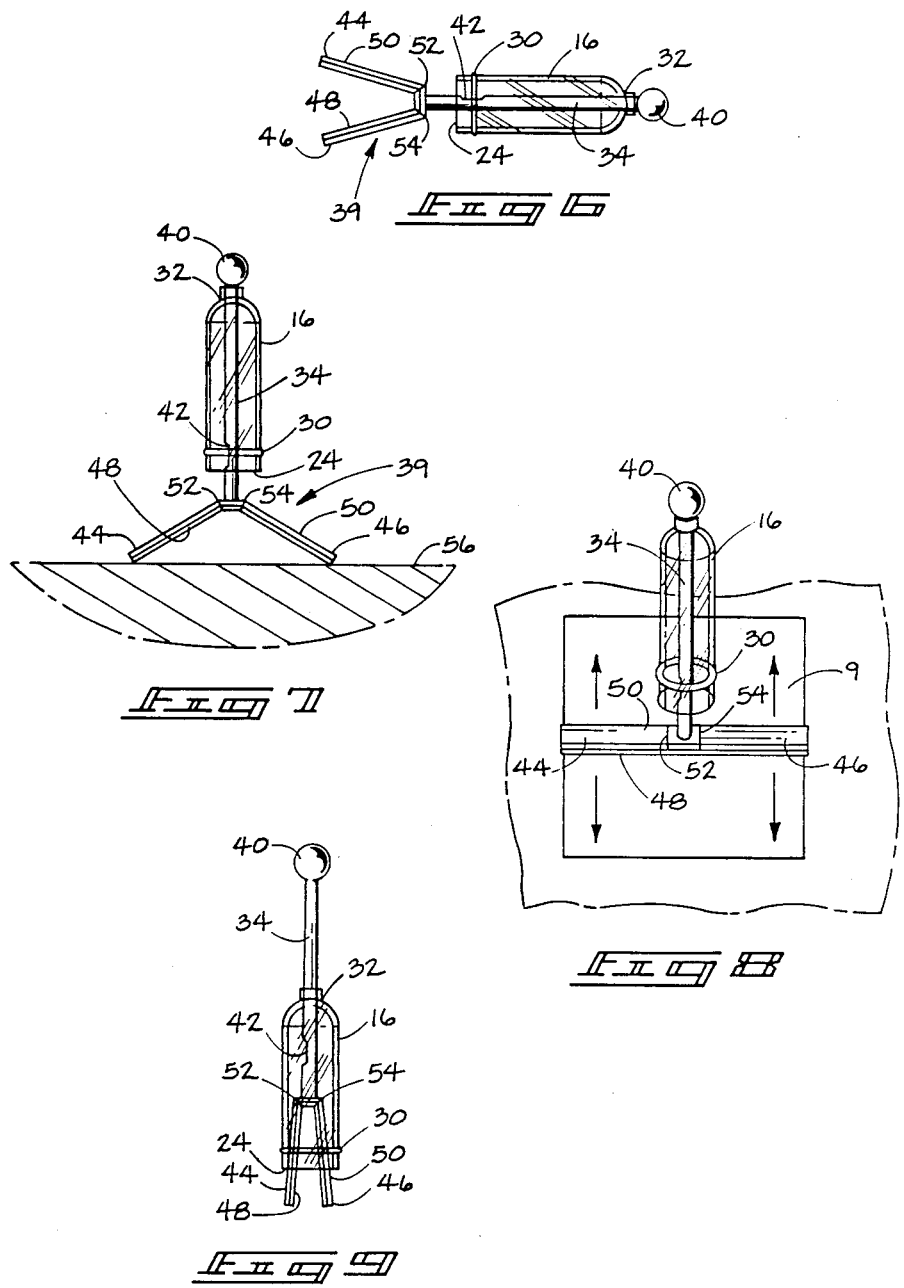

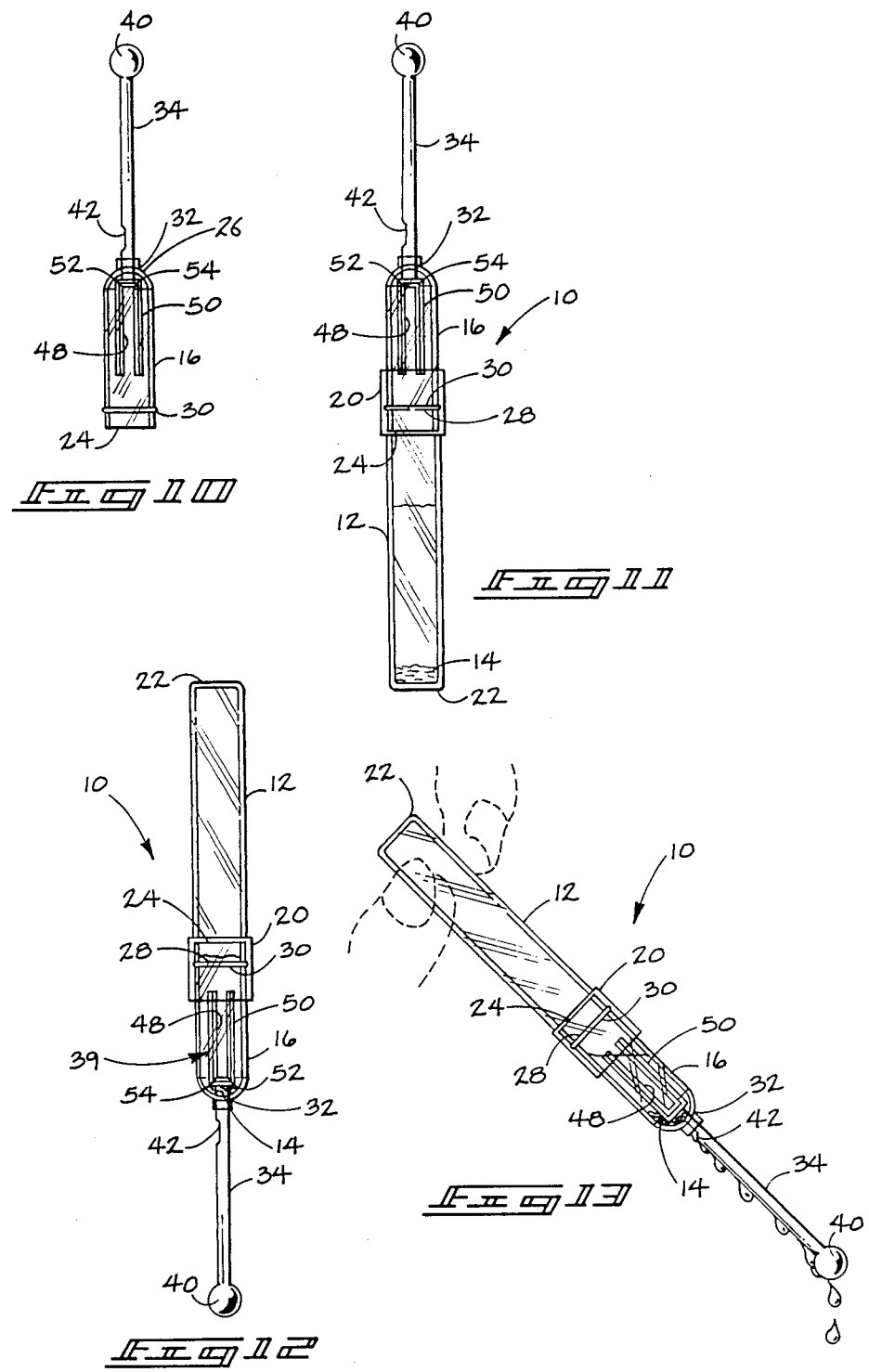

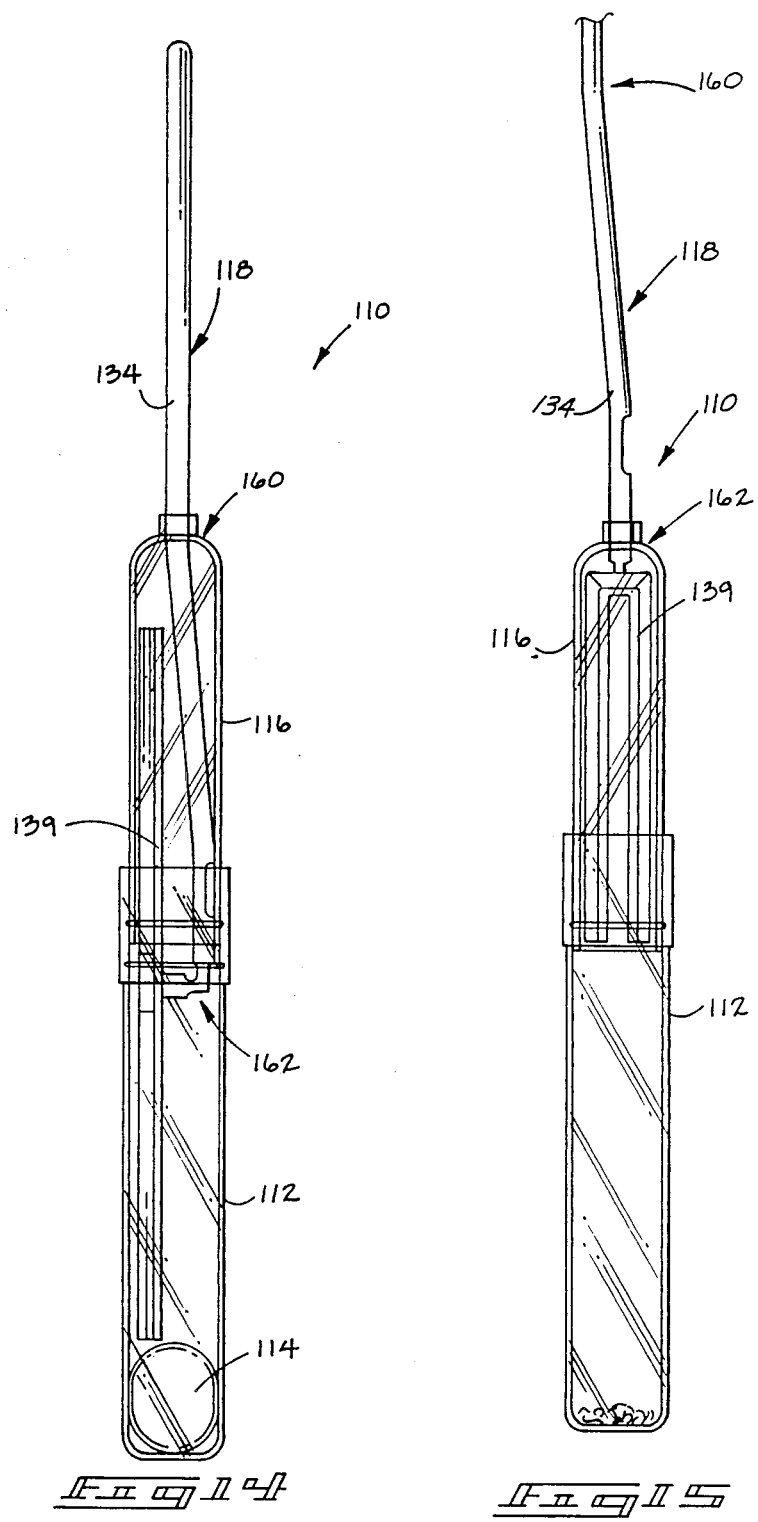

1

SAMPLING APPARATUS

BACKGROUND OF THE INVENTION

This invention was made with government support under Contract No. DE-AC06-76RLO 1830 awarded by the U.S. Department of Energy. The government has certain rights to the invention.

TECHNICAL FIELD

This invention relates to methods and apparatus for sampling substances from solid surfaces.

The invention arose out of the needs and concerns associated with sampling toxic agents, such as T-2 toxin. As will be apparent from the discussion, apparatus in accordance with the invention will be useful in sampling any substances from a solid surface, regardless of the toxicity of the substance.

One of the present concerns with sampling toxic substances from solid surfaces includes collecting a sufficient quantity of the substance from a defined area to qualitatively determine composition. The substance must also be collected in a manner that minimizes risk of exposure to the sample by the person doing the sampling. Also, under many government regulated protocols, defined areas of surfaces are sampled in an effort to obtain some quantitative as well as qualitative analysis of the toxic substance that is present. This invention is directed to improvements in sampling substances from solid surfaces.

BRIEF DESCRIPTION OF THE DRAWINGS

Preferred embodiments of the invention are illustrated in the accompanying drawings, in which:

FIG. 1 is a longitudinal, partial section view of a sampling apparatus in accordance with the invention.

FIG. 2 is a side elevational view of one body component of the apparatus of FIG. 1.

FIG. 3 is a side elevational view of another body component of the apparatus of FIG. 1.

FIG. 4 is a side elevational view of still another component of the apparatus of FIG. 1.

FIGS. 5-13 are sequential operational views illustrating use of the sampling apparatus of FIG. 1 in sampling substances from solid surfaces.

FIG. 14 is a side elevational view of an alternative embodiment sampling apparatus in accordance with the invention.

FIG. 15 is a side elevational view of components of the apparatus of FIG. 14 shown in one operational configuration.

DETAILED DESCRIPTION OF PREFERRED EMBODIMENTS

The following disclosure of the invention is submitted in complicance with the constitutional purpose of the Patent Laws "to promote the progress of science and useful arts" (Article 1, Section 8).

Referring to FIGS. 1-4, a preferred embodiment sampling apparatus in accordance with the invention is indicated generally by reference numeral 10. Sampler 10 is comprised of four primary components. These are a first tubular body 12, a frangible ampoule 14, a second tubular bofdy 16, and a sample extractor 18. These four components cooperably interconnect and are provided to a user in the form shown in FIG. 1.

More particularly, first tubular body 12 is elongated and circular in lateral cross-section. It has an open inner or first end 20 and a closed outer or second end 22 which define a longitudinal length. Second tubular body 16 is also elongated and circular in lateral cross-section. It has an inner or first end 24 and an outer or second end 26 which define a second body longitudinal length. In the depicted embodiment, first tubular body 12 is longer than second tubular body 16. The inner end 24 of the second body 16 is open and sized and configured for fluid sealing engagement with inner end 20 of the first body 12. As illustrated, first and second bodies 12, 16 respectively telescopically engage one another, with second body open end 24 being internally received within first body open end 20.

An interlocking groove 28 is formed at inner end 20 of first body 12. A complementary interlocking radially projecting ring 30 is formed on the inner end 24 of second body 16. Ring 30 is sized and positioned for selective interlocking receipt within interlocking groove 28. A substantially fluid-tight seal is therefor formed between open ends 20, 24 of first and second bodies 12, 16 respectively, when the same are telescopically received relative to one another. In the depicted and preferred embodiment, the fluid tight seal is maintained regardless of receipt by ring 30 within groove 28. Although groove 28 is illustrated as being formed in first body 12 and projecting ring 30 is illustrated as being formed in second body 16, this configuration could of course be reversed without departing from the principles and scope of the invention. Of primary importance is the formation of a fluid sealing engagement of the inner ends of the first and second bodies.

FIG. 1 illustrates first and second bodies 12, 16 interconnected with one another, with ring 30 being longitudinally displaced from groove 28.

Outer end 26 of second body 16 includes a tubular passageway 32 which extends therethrough. Passageway 32 includes walls of a predetermined length and operably engages with sample extractor 18 as described below.

Extractor 18 includes a rod 34 having an internal or first end 36 and an external or second end 38 which define a longitudinal length. The length of rod 34 is greater than the length of second tubular body 16. Inner rod end 36 supports an absorbent pad assembly 39, while external rod end 38 supports a radially projecting handle portion 40. Rod 34 is slidably and rotatably received within second body passageway 32.

Means are provided for controlling egress of fluid from first and second tubular bodies 12, 16 when the same are in fluid sealing engagement relative to one another, such as shown in FIG. 1. This means is preferably provided by the relationship of the diameter of shaft 34 and the diameter of passageway 32. First, the diameters are such that engagement of rod 34 relative to passageway 32 is of a sufficiently tight tolerance to permit sliding of rod 34 relative to passageway 32, yet prevent flow of liquid through passageway 32 and around rod 34. As an example, where the passageway has a diameter of 0.188 inches, a rod diameter of the same dimension will provide no clearance to a slight inference which gives a tight sliding fit.

Second, a recess 42 is formed along the length of the rod preferably at a location longitudinally displaced from absorbent pad 39. Recess 42 has a longitudinal length at least as great as the length of the passageway walls. With such a configuration, a substantially fluid tight seal is maintained when recess 42 and passageway 32 are longitudinally displaced from one another (FIG. 1). However, flow of liquid through passageway 32 and around rod 34 is accommodated when rod recess 42 and passageway 32 are positioned longitudinally coincident (FIG. 13), as will be explained more fully below.

As is illustrated by FIGS. 1 and 4, absorbent pad assembly 39 is mounted for two primary orientations relative to rod 34 and the telescopically engaged first and second bodies 12, 16. FIG. 4 illustrates mounting of pad assembly 39 for lateral orientation relative to rod 34 to form a general T-shape therewith. Pad assembly 39 forms two T arms 44, 46, with rod 34 forming a T-stem. FIG. 1 illustrates that pad assembly 39 is foldably retractable within second tubular body 16 to generally longitudinally orient a substantial portion of T arms 44, 46 with second tubular body 16 and rod 34.

Pad assembly 39 is comprised of an absorbent material 48 which is mounted or adhered to a non-absorbent and firmer backing 50. A pair of indentations 52, 54 are formed in the surface of backing 50 against which absorbent material 48 is adhered. Indentations 52, 54 function as hinges or flex points which accommodate folding and retraction of pad assembly 39 within second tubular body 16, as illustrated in FIG. 1. These hinges 52, 54 are positioned radially inward relative to the second body walls to facilitate the folding and retraction.

FIG. 1 illustrates that frangible ampoule 14 is retained within first tubular body 12. Arms 44, 46 of absorbent pad assembly 39 are positioned to contact the inner end of ampoule 14 to prevent it from sliding within the interconnected first and second bodies. Ampoule 14 contains a suitable solvent for collecting whatever substance is being sampled. For purposes of this disclosure, the term "solvent" refers to any fluid capable of at least partially dissolving or suspending in solution a substance being sampled. Ampoule 14 is preferably made of any frangible substance which is substantially impermeable to the solvent it contains.

The side walls of first tubular body 12 are constructed to be sufficiently flexible to accommodate crushing of frangible ampoule 14 by inwardly compressing the first tubular body (FIG. 5). Alternate means for accommodating breakage of the ampoule could of course also be provided. For example, a pointed object could be provided inside of the first and second bodies which would selectively engage the ampoule to cause its breakage.

MATERIALS AND MANUFACTURE

First and second bodies 12, 16, extractor handle 40, rod 34 and nonabsorbent backing 50 are preferably injection molded using a transparent or translucent polypropylene homopolymer. An example is Marlex 7042 polypropylene available from the Phillips Chemical Company of Pasadena, Tex.

Preferably, nonabsorbent backing 50 and rod 34 are injection molded as one piece. An absorbent material, such as felt, is then bonded to backing 50 using an appropriate adhesive, such as Silastic 732 adhesive, available from the Dow-Corning Corporation of Midland, Mich., after the bonding surface has been activated with an open flame or other suitable procedure. The T arms 44, 46 are then folded about hinges 52, 54, and rod 34 inserted through second body 16 and passageway 32. Handle 40 is then attached to rod 34 by an adhesive or welding. With such a construction, handle 40 prevents rod 34 from moving entirely inwardly through passageway 32, while absorbent pad assembly 39 prevents rod 34 from moving entirely outwardly through passageway 32.

A frangible ampoule 14 with a suitable solvent is then inserted into first body 12, and then first and second bodies 12, 16 engaged as shown in FIG. 1. Any solvent capable of dissolving or at least partially suspending the substance being sampled would be usable. For sampling of T-2 toxin, a 10 percent methanol solution (the remainder being water) was determined to be the preferred solvent for a wide variety of operating and storage conditions.

OPERATION

A description of the operation of the illustrated sampler proceeds with reference to FIGS. 1 and 5–13. Immediately prior to use, sampler 10 will appear as illustrated in FIG. 1. This illustrates the sampler in a partially locked mode. First and second body halves are telescopically engaged relative to one another, but second body 16 is not received far enough into first body 12 such that locking ring 30 and grooves 28 engage. In this mode, a fluid tight seal is maintained between the first and second bodies, yet the first and second bodies are easily separated from one another. When second body 16 is pushed into first body 12 in the fully locked mode, ring 30 engages with groove 28, also providing a fluid tight seal. In the fully locked mode, the second body 16 is still removable from first body 12, but with greater difficulty than in the partially locked mode.

A flexible plastic sleeve or tube sized to fit around sampler 10 (not shown) is slipped over sampler 10. The side walls of first body 12 are then squeezed to crush and shatter ampoule 14 (FIG. 5). The flexible tube will protect the user's fingers in the unlikely event of first body 12 breaking or leaking when ampoule 14 is crushed. Preferably during this crushing operation, sampler 10 is kept from bending to minimize any chances of cracking first body 12, or inadvertently pulling first body 12 from the second body 16.

Upon breaking of ampoule 14, the flexible tubing is removed. Sampler 10 is then tilted to allow solvent from the broken ampoule to flow onto felt 48.

After wetting felt 48, sampler 10 is turned vertically such that first body 12 is beneath second body 16. First and second bodies 12, 16 are then separated. Handle 40 is grasped and pushed inwardly until it bears against the outer opening of passageway 32 to push wiping arms 44, 46 out of second body inner end 24 (FIG. 6). Wiping arms 44, 46 are then pressed against a surface 56 from which a sample is to be collected (FIG. 7). Pressing is continued until arms 44, 46 extend laterally out from rod 34, and the wiping surfaces of felt material 48 are completely against the area being sampled. The area to be sampled is then wiped with the extractor by rubbing back and forth smoothly for approximately 15 seconds to solubilize or otherwise collect the material being sampled. The sampled area preferably defines a square 9 that is the combined width of sampler arms 44, 46 and equally as long (FIG. 8). Standardizing of sampling technique in such a manner will enable some quantitative in addition to qualitative analysis of the substance.

When rubbing is complete, felt material 48 is used to soak up as much of any solvent that remains from the sampled area. Then arms 44, 46 are retracted back into second body 16 by pulling on handle 40 (FIG. 9). Arms 44, 46 will fold and can be pulled into second body 16 to the point where the nonabsorbent backing bears internally against second body end 26 (FIG. 10). While maintaining first body 12 substantially vertical with its open end 20 up, inner end 24 of second body 16 is pushed into first body 12 until groove 28 and ring 30 engage into the fully locked position (FIG. 11). In such position, handle recess 42 will be outside of second body 16 and fully beyond passageway 32.

The sampler is then vertically inverted such that second body 16 is beneath first body 12 (FIG. 12). Solvent will be prevented from leaking through passageway 32 and around rod 34 because of the fluid tight seal maintained therebetween. Handle 40 is then twisted back and forth four or five times to agitate the wiping arms back and forth within the solvent to fully dissolve, or suspend, and mix the substance which was collected on wiping arms 44, 46. Displacement of recess 42 from pad assembly 39, as illustrated by the preferred embodiment, enables the pad to function as a stirrer at the bottom-most portion of the solvent.

Sampler 10 is then tilted and rod 34 pushed into second body 16 until recess 42 and passageway 32 are longitudinally coincident (FIG. 13). Alternately, rod 34 is pushed into second body 16 until recess 42 and passageway 32 are longitudinally coincident, and then the sampler is tilted. This provides a gap through passageway 32 and over rod 34 enabling solvent to leak from first and second bodies 12, 16, and drip down along rod 34 and over handle 40. The sides of the sampler can be squeezed until the desired number of drops have been dispensed and collected into a suitable test container. The angle with which sampler 10 is maintained during dispensing and degree of squeezing by the user will control solvent flow rate. After this is complete, the sampler can be discarded.

The sampler has been determined to work best when extracting substances from smooth and fairly flat surfaces. Samples can be collected from dry, moist, mist coated or dewy surfaces, but preferably areas having large drops or puddles are avoided.

The device as constructed and described was primarily intended for sampling T-2 toxin. However, other toxic substances could also be sampled, such as for example carcinogens, pesticides, herbicides, etc. Furthermore, the material being sampled could be non-toxic. The solvent within the frangible ampoule would be designed according to what is being sampled.

The collected sample would also be amenable to many sampling techniques as for example, gas chromatography, liquid chromatography, fluorometers or other measurement systems.

EXAMPLE OF AN ALTERNATE EMBODIMENT

FIGS. 14 and 15 illustrate an alternate embodiment sampling apparatus 110. Sampler 110 is similar to sampler 10 in that it includes a first body 112, second body 116, ampoule 114, and extractor 118. The primary differences between sampler 110 and sampler 10 relate to extractor 118 and the longitudinal length of first and second bodies 112, 116. FIG. 14 illustrates that absorbent pad assembly 139 is longitudinally oriented lengthwise within joined first and second bodies 112, 116. Extractor rod 134 is permanently bent slightly at location 160, and recessed and bent 90 degrees at location 162 to connect with and provide space for retaining absorbent pad 139 in the illustrated manner. Because of this lengthwise orientation, the respective length of each of the first and second bodies 112, 116 are somewhat longer than in the first embodiment to accommodate the stretched out version of pad assembly 139.

Also, frangible ampoule 114 takes on an alternate shape, as absorbent pad assembly 139 extends into first body 112.

FIG. 15 illustrates that after sampling operation is complete, the arms are foldably retractable within second body 116.

In compliance with the statute, the invention has been described in language more or less specific as to structural features. It is to be understood, however, that the invention is not limited to the specific features shown, since the disclosed means and construction comprise preferred forms of putting the invention into effect. The invention is, therefore, claimed in any of its forms or modifications within the proper scope of the appended claims, appropriately interpreted in accordance with the doctrine of equivalents.

We claim:

1. An apparatus for sampling substances from solid surfaces comprising:
   a first tubular body having a longitudinal length extending between an open first end and a closed second end;
   a frangible ampoule retained within the first tubular body, the ampoule containing a solvent capable of at least partially dissolving or suspending a substance to be sampled;
   a second tubular body havng a longitudinal length extending between a first end and a second end, the first end of the second tubular body being open and being sized and configured for fluid sealing engagement with the first end of the first tubular body, the second tubular body second end including a passageway formed therethrough, the passageway having walls of a predetermined length;
   a rod slidably received within the passageway fromed through the second end of the second body, the rod having a longitudinal length extending between a first end and a second end, the length of the rod being greater than the length of the second tubular body;
   an absorbent pad at the first end of the rod; and
   a recess formed along the length of the rod, the recess having a longitudinal length at least as great as the length of the passageway walls to accommodate flow of fluid through the passageway and around the rod when the rod recess and passageway are positioned longitudinally coincident.

2. The apparatus of claim 1 wherein the absorbent pad comprises felt.

3. The apparatus of claim 1 wherein the rod includes a radially projecting portion adjacent its second end to prevent the rod from moving entirely inwardly through the passageway, the absorbent pad preventing the rod from moving entirely outwardly through the passageway.

4. The apparatus of claim 1 wherein the recess is formed in the rod surface at a location longitudinally displaced from the absorbent pad.

5. The apparatus of claim 4 wherein the rod includes a radially projecting portion adjacent its second end to prevent the rod from moving entirely inwardly through the passageway, the absorbent pad preventing the rod from moving entirely outwardly through the passageway.

6. The apparatus of claim 1 wherein,
   the first ends of the first and second bodies telescopically engage one another;

an interlocking groove being formed at the first end of one of the first or second body;

a complementary interlocking radially projecting ring being formed at the first end of the other of the first or second body, such ring being sized and positioned for selective interlocking receipt within the interlocking groove upon telescopic engagement of the first and second bodies; and a substantially fluid tight seal being formed between the open ends of the first and second bodies when the same are telescopically engaged, regardless of receipt of the ring by the groove.

7. The apparatus of claim 1 wherein, the first ends of the first and second bodies telescopically engage one another;

an interlocking groove being formed at the first end of one of the first or second body;

a complementary interlocking radially projecting ring being formed at the first end of the other of the first or second body, such ring being sized and positioned for selective interlocking receipt within the interlocking groove upon telescopic engagement of the first and second bodies; and a substantially fluid tight seal being formed between the open ends of the first and second bodies when the same are telescopically engaged, regardless of receipt of the ring by the groove.

8. The apparatus of claim 7 wherein the rod includes a radially projecting portion adjacent its second end to prevent the rod from moving entirely inwardly through the passageway, the absorbent pad preventing the rod from moving entirely outwardly through the passageway.

9. The apparatus of claim 8 wherein the recess is formed in the rod surface at a location longitudinally displaced from the absorbent pad.

10. The apparatus of claim 1 wherein the rod is rotatably as well as slidably received by the passageway.

11. An apparatus for sampling substances from solid surfaces comprising:

a first tubular body having a longitudinal length extending between an open first end and a closed second end;

a frangible ampoule retained within the first tubular body, the ampoule containing a solvent capable of at least partially dissolving or suspending a substance to be sampled;

a second tubular body having a longitudinal length extending between a first end and a second end, the first end of the second body being open and being sized and configured for fluid sealing engagement with the first end of the first tubular body, the second tubular body second end including a passageway formed therethrough, the passageway having walls of a predetermined length;

a rod slidably received within the passageway formed through the second end of the second body, the rod having a longitudinal length extending between a first end and a second end, the length of the rod being greater than the length of the second tubular body;

an absorbent pad at the first end of the rod, the pad being mounted for lateral orientation relative to the rod to form an expanded general T shape therewith, the absorbent pad forming arms of the expanded general T shape with the rod forming a T stem, the absorbent pad being foldably retractable within the second tubular body to longitudinally orient at least a substantial portion of the arms with the second tubular body and rod; and means for controlling egress of fluid from the first and second tubular bodies when such are in fluid sealing engagement relative to one another.

12. The apparatus of claim 11 wherein the absorbent pad comprises an absorbent material mounted to a non-absorbent backing, the material and backing being foldably retractable within the second tubular body.

13. The apparatus of claim 12 wherein folding of the non-absorbent backing is accommodated by a pair of hinges formed therein.

14. The apparatus of claim 13 wherein, the second tubular body includes body walls; and the hinges each comprise a depression formed in the non-absorbent backing, the depressions being positioned radially inward of the second body walls.

15. The apparatus of claim 11 wherein the absorbent pad comprises felt.

16. The apparatus of claim 11 wherein the rod includes a radially projecting portion adjacent its second end to prevent the rod from moving entirely inwardly through the passageway, the absorbent pad preventing the rod from moving entirely outwardly through the passageway.

17. The apparatus of claim 11 wherein, the first ends of the first and second bodies telescopically engage one another;

an interlocking groove being formed at the first end of one of the first or second body;

a complementary interlocking radially projectiang ring being formed at the first end of the other of the first or second body, such ring being sized and positioned for selective interlocking receipt within the interlocking groove upon telescopic engagement of the first and second bodies; and a substantially fluid tight seal being formed between the open ends of the first and second bodies when the same are telescopically engaged, regardless of receipt of the ring by the groove.

18. The apparatus of claim 17 wherein the absorbent pad comprises an absorbent material mounted to a non-absorbent backing, the material and backing being foldably retractable within the second tubular body.

19. The apparatus of claim 17 wherein the rod includes a radially projecting portion adjacent its second end to prevent the rod from moving entirely inwardly through the passageway, the absorbent pad preventing the rod from moving entirely outwardly through the passageway.

20. The apparatus of claim 17 wherein the rod is rotatably as well as slidably received by the passageway.

21. The apparatus of claim 11 wherein the rod is rotatably as well as slidably received by the passageway.

22. The apparatus of claim 11 wherein the means for controlling egress of fluid comprises:

a recess formed along the length of the rod, the recess having a longitudinal length at least as great as the length of the passageway walls, a substantially fluid tight seal being maintained when the recess and passageway are longitudinally displaced from one another, flow of fluid through the passageway and around the rod being accommodated when the rod recess and passageway are positioned longitudinally coincident.

23. The apparatus of claim 22 wherein the recess is formed in the rod surface at a location longitudinally displaced from the absorbent pad.

24. The apparatus of claim 23 wherein the rod is rotatably as well as slidably received by the passageway.

25. The apparatus of claim 22 wherein the absorbent pad comprises an absorbent material mounted to a non-absorbent backing, the material and backing being sufficiently flexible to accommodate folding and retraction of the pad within the second tubular body.

26. The apparatus of claim 25 wherein folding of the non-absorbent backing is accommodated by a pair of hinges formed therein.

27. The apparatus of claim 26 wherein,
the second tubular body includes body walls; and
the hinges each comprise a depression formed in the non-absorbent backing, the depressions being positioned radially inward of the second body walls.

28. The apparatus of claim 22 wherein the rod includes a radially projecting portion adjacent its second end to prevent the rod from moving entirely inwardly through the passageway, the absorbent pad preventing the rod from moving entirely outwardly through the passageway.

29. The apparatus of claim 22 wherein,
the first ends of the first and second bodies telescopically engage one another;
an interlocking groove being formed at the first end of one of the first or second body;
a complementary interlocking radially projecting ring being formed at the first end of the other of the first or second body, such ring being sized and positioned for selective interlocking receipt within the interlocking groove upon telescopic engagement of the first and second bodies; and
a substantially fluid tight seal being formed between the open ends of the first and second bodies when the same are telescopically engaged, regardless of receipt of the ring by the groove.

30. The apparatus of claim 29 wherein,
the recess is formed in the rod surface at a location longitudinally displaced from the absorbent pad;
the absorbent pad comprises an absorbent felt mounted to a non-absorbent backing, the felt and backing being sufficiently flexible to accommodate folding and retraction of the pad within the second tubular body; and
the rod includes a radially projecting portion adjacent its second end to prevent the rod from being slid entirely through the passageway in the direction of the rod first end, the absorbent pad preventing the rod from being slid entirely through the passageway in the direction of the rod second end.

31. The apparatus of claim 22 wherein the rod is rotatably as well as slidably received by the passageway.

32. An apparatus for sampling substances from solid surfaces comprising:
a first tubular body having a longitudinal length extending between an open first end and a closed second end;
a frangible ampoule retained within the first tubular body, the ampoule containing a solvent capable of at least partially dissolving or suspending a substance to be sampled;
a second tubular body havng a longitudinal length extending between a first end and a second end, the first end of the second tubular body being open and being sized and configured for fluid sealing engagement with the first end of the first tubular body, the second tubular body second end including a passageway formed therethrough, the passageway having walls of a predetermined length;
the first ends of the first and second bodies being telescopically engaged relative to one another, an interlocking groove being formed at the first end of one of the first or second body, a complementary interlocking radially projecting ring being formed in the first end of the other of the first or second body, such ring being sized and positioned for selective interlocking receipt within the interlocking groove, a substantially fluid tight seal being formed between the open ends of the first and second bodies regardless of receipt of the ring by the groove;
a rod slidably and rotatably received within the passageway formed through the second end of the second body, the rod having a longitudinal length extending between a first end and a second end, the length of the rod being greater than the length of the second tubular body;
an absorbent pad at the first end of the rod, the pad being mounted for lateral orientation relative to the rod to form a an expanded general T shape therewith, the absorbent pad forming arms of the expanded general T shape with the rod forming a T stem, the absorbent pad being foldably retractable within the second tubular body to longitudinally orient at least a substantial portion of the arms with the second tubular body and rod, the absorbent pad comprising an absorbent felt material mounted to a non-absorbent backing, the material and backing being foldably retractable within the second tubular body, folding of the non-absorbent backing being accommodated by a pair of hinges formed therein;
a recess formed along the length of the rod at a location longitudinally displaced from the absorbent pad, the recess having a longitudinal length at least as great as the length of the passageway walls, a substantially fluid tight seal being maintained when the recess and passageway are longitudinally displaced from one another, flow of fluid through the passageway and around the rod being accommodated when the rod recess and passageway are positioned longitudinally coincident; and
the rod including a radially projecting portion adjacent its external second end to prevent the rod from moving entirely inwardly through the passageway, the absorbent pad preventing the rod from moving entirely outwardly through the passageway.

* * * * *